United States Patent [19]

Furutani et al.

[11] Patent Number: 5,589,596

[45] Date of Patent: Dec. 31, 1996

[54] PROCESS FOR PRODUCING AMINES

[75] Inventors: Atsushi Furutani, Nishinomiya; Takuo Hibi, Toyonaka; Michio Yamamoto, Otsu; Kazuyuki Tanaka, Ibaraki; Kazuhiro Tada, Kyoto; Masami Fukao, Kurita-gun; Gohfu Suzukamo, Suita, all of Japan

[73] Assignee: Sumitomo Chemical Company, Limited, Osaka, Japan

[21] Appl. No.: 194,328

[22] Filed: Feb. 8, 1994

[30] Foreign Application Priority Data

| Apr. 27, 1993 | [JP] | Japan | 5-101074 |
| Jul. 21, 1993 | [JP] | Japan | 5-180248 |
| Jul. 21, 1993 | [JP] | Japan | 5-180249 |
| Aug. 6, 1993 | [JP] | Japan | 5-196041 |
| Aug. 9, 1993 | [JP] | Japan | 5-197339 |

[51] Int. Cl.⁶ .................................... C07C 209/22
[52] U.S. Cl. .................. 564/446; 546/244; 548/408
[58] Field of Search .................. 564/446, 248; 546/244; 548/411, 408

[56] References Cited

U.S. PATENT DOCUMENTS

| 4,041,080 | 8/1977 | Göthel et al. | 564/375 |
| 4,206,149 | 6/1980 | Slaugh | 564/479 |
| 4,206,150 | 6/1980 | Slaugh | 564/480 |
| 4,429,157 | 1/1984 | Disteldorf et al. | 564/446 |
| 4,487,966 | 12/1984 | Fiedler et al. | 564/454 |
| 5,132,427 | 7/1992 | Koehler et al. | 546/246 |
| 5,166,396 | 11/1992 | Hutchmacher et al. | 558/431 |
| 5,166,444 | 11/1992 | Hutchmacher et al. | 564/491 |
| 5,239,120 | 8/1993 | Merger et al. | 564/454 |
| 5,286,906 | 2/1994 | Hara et al. | 564/446 |

FOREIGN PATENT DOCUMENTS

| 2039328 | 10/1991 | Canada . |
| 0394968 | 10/1990 | European Pat. Off. . |
| 0394967 | 10/1990 | European Pat. Off. . |
| 0424738 | 5/1991 | European Pat. Off. . |
| 0503246 | 9/1992 | European Pat. Off. . |
| 0534449 | 3/1993 | European Pat. Off. . |
| 0530696 | 3/1993 | European Pat. Off. . |
| 1518118 | 10/1964 | Germany . |
| 0449089 | 10/1991 | Japan . |
| 5-279303 | 10/1993 | Japan . |
| 5-301847 | 11/1993 | Japan . |
| 972010 | 10/1964 | United Kingdom . |
| 1554516 | 10/1979 | United Kingdom . |

OTHER PUBLICATIONS

Koike et al. "Chemical Abstracts" vol. 80, 1974—p. 384 (abstract No. 145377g).
Huthmacher et al. Chem. Abs. 118:38503j, Sep.1992.
Derwent Pub., Ltd., week 7119, Class A43, AN 71–31600S and JP 46016723 (1967).

*Primary Examiner*—Brian M. Burn
*Attorney, Agent, or Firm*—Birch, Stewart, Kolasch & Birch, LLP

[57] ABSTRACT

A process is disclosed for producing an amine by carrying out a reductive amination of a cyclic ketone or by carrying out a reduction of an imino derivative of a cyclic ketone to the corresponding amine which process is characterized in using a cobalt catalyst containing a carbonate of an alkaline earth metal and/or lanthanum oxide.

32 Claims, No Drawings

PROCESS FOR PRODUCING AMINES

The present invention relates to a process for producing amines, and more particularly, to a process for producing amines by carrying out a reductive amination of a cyclic ketone or by carrying out a reduction of an imino derivative of a cyclic ketone to the corresponding amine which comprises using a cobalt catalyst containing a carbonate of an alkaline earth metal and/or lanthanum oxide.

Amines are useful as intermediates for fine chemicals and raw materials for resins, and are well known to be produced by a reductive amination of a cyclic amine or by reduction of an imino derivative of a cyclic ketone.

For example, for the production of 3-aminomethyl-3,5,5-trimethylcyclohexylamine (IPDA) by a reductive amination of 3-cyano-3,5,5-trimethylcyclohexanone (IPCN), the following processes have been known:

(1) a cobalt catalyst supported on silicic acid is used (BP 972010) and (2) a Raney-cobalt catalyst is used (Japanese Patent 62-123154A).

Also, as processes for producing IPDA by reducing an imino derivative of IPCN, the following processes have been known:

(3) a cobalt catalyst is used (U.S. Pat. No. 4429157) and (4) a ruthenium catalyst supported on alumina is used (Japanese Patent 4-221350A).

However, the yield of the amine to be produced is not sufficiently high in any of the processes mentioned above, and thus, improvements in the yield has been desired.

As a result of the diligent research on catalysts to develop a more excellent process for producing amines, it has now been found that a specific cobalt catalyst containing a carbonate of an alkaline earth metal and/or lanthanum oxide not only increases the yield of amines but also exhibits a high catalyst activity to efficiently provides amines with a small amount of a catalyst, and as a result of further study, the present invention was accomplished.

An object of the present invention is to provide a process which is excellent in commercial scale for producing an amine by carrying out a reductive amination of a cyclic ketone or by carrying out a reduction of an imino derivative of a cyclic ketone to the corresponding amine which comprises using a cobalt catalyst containing a carbonate of an alkaline earth metal and/or lanthanum oxide.

The present invention will be explained hereinafter in more detail.

The present invention is characterized in that a cobalt catalyst containing a carbonate of an alkaline earth metal and/or lanthanum oxide is used.

The carbonate of an alkaline earth metal includes a carbonate of, for example, magnesium, calcium, strontium, or barium, with preferred being calcium carbonate.

The weight ratio of the alkaline earth metal and/or lanthanum oxide to metal cobalt is usually 10/90 to 98/2.

Also, the cobalt catalyst used in the present invention preferably contains copper, ruthenium, or an alkali metal compound, and more preferably contains copper and/or ruthenium and an alkali metal compound in addition to the carbonate of an alkaline earth metal and/or lanthanum oxide.

The catalyst used in the present invention can easily be prepared by a precipitation method, coprecipitation method, mixing method, or impregnation and deposition method, and the precipitation method and coprecipitation method are preferable.

As typical examples, methods for producing a cobalt catalyst containing a carbonate of an alkaline earth metal, copper and/or ruthenium, and an alkali metal compound are described.

In the precipitation method, for instance, a carbonate of an alkaline earth metal is suspended in a solution in which a cobalt salt and copper salt and/or ruthenium salt are dissolved; a solution of an alkali is added to the suspension to precipitate the cobalt and copper and/or ruthenium on the carbonate of an alkaline earth metal such that the former catalyst components are supported on the latter catalyst component; the solid is filtered, washed, and then mixed with a solution of an alkali metal compound; the solvent of the solution is evaporated; and then the solid is dried, calcined, and reduced with hydrogen.

When the solution of an alkali is a solution of an alkali metal compound, a catalyst can be prepared as follows. A moderate content of the alkali metal compound is left in the precipitate by adjusting the washing and other conditions after filtration, and the precipitate is dried, calcined, and reduced with hydrogen.

As the cobalt salt, copper salt, and ruthenium salt, water soluble salts such as their nitrates, sulfates, and halides, organic acid salts can be mentioned. When an organic solvent such as methanol is used, a complex compound such as cobalt carbonyl and ruthenium carbonyl can also be used.

As the alkali, for example, carbonates, hydroxides, hydrogencarbonates, or organic acid salts of alkali metals, ammonium carbonate, and aqueous ammonia can be mentioned. As the alkali metal compound, carbonates, nitrates, hydroxides, and hydrogencarbonates of alkali metals can be mentioned. The alkali metals include lithium, sodium, potassium, rubidium, and cesium.

These alkalis are generally used as an aqueous solution, solution of an organic solvent such as methanol, or mixed solution thereof.

The temperature at which the cobalt and copper and/or ruthenium are precipitated and supported on the carbonate of an alkaline earth metal is usually in a range of room temperature to 100° C.

The calcination of the catalyst components precipitated and supported on the carbonate is usually carried out in a nitrogen gas stream at a temperature from 300° to 500° C. for about 30 minutes to about 5 hours, and the hydrogen reduction is usually carried out at a temperature of 200° to 500° C. for about 30 minutes to about 20 hours.

In the coprecipitation method, for instance, a solution of an alkali such as a carbonate of an alkali metal and ammonium carbonate is added to a mixed solution of a cobalt salt, copper salt and/or ruthenium salt, and a salt of an alkaline earth metal to form a coprecipitate, and the coprecipitate is filtered, washed, and mixed with a solution of an alkali metal compound. Then, the solvent of the solution is evaporated and the solid is dried, calcined, and reduced with hydrogen.

When the solution of an alkali is a solution of an alkali metal compound, a catalyst can be prepared as follows. A moderate content of an alkali metal compound is left in the precipitate by adjusting washing and other conditions after filtration and the precipitate is dried, calcined, and reduced with hydrogen.

As the cobalt salt, copper salt, and ruthenium salt, such salts and complex compounds as described above can be mentioned. As the salt of an alkaline earth metal, nitrates and halides of alkaline earth metals can be used.

Also, as the alkali and alkali metal compounds, the same compounds as described above can be mentioned.

The conditions for forming a precipitate, and for calcination and hydrogen reduction are usually the same as in the method described above.

In the mixing method, for instance, a solution of an alkali is added to a solution of a cobalt salt and a copper salt and/or ruthenium salt to form a precipitate, a carbonate of an alkaline earth metal is added to the solution, the precipitate and carbonate are mixed and filtered, washed, and then mixed with a solution of an alkali metal compound. Then the solvent of the solution is evaporated and the solid is dried, calcined, and reduced with hydrogen. When the solution of an alkali is a solution of an alkali metal compound, a catalyst can be produced as follows. A moderate content of the alkali metal compound is left in the precipitate by adjusting the washing and other conditions after filtration and the precipitate is dried, calcined, and reduced with hydrogen.

As the cobalt salt, copper salts and ruthenium salt, the same salts and complex compounds as described above can be mentioned. As the alkali and alkali metal compound, the same ones as mentioned above can be mentioned.

The conditions for forming a precipitate, and for calcination and hydrogen reduction are usually the same as those described above.

In the impregnation and deposition method, for instance, a carbonate of an alkaline earth metal is impregnated with a solution in which a cobalt salt and a copper salt and/or ruthenium salt are dissolved, and then the salts are dried, calcined at a temperature higher than the thermal degradation temperature of the salts, mixed with a solution of an alkali metal compound. Then, the solvent of the solution is evaporated and the solid thus precipitated is dried, calcined, and with reduced hydrogen.

As the cobalt salt, copper salt, and ruthenium salt, the same salts as described above can be mentioned. As the alkali metal compound, the same ones as described above can be used.

The calcination of the salt impregnated and deposited on the supporter is usually performed at a temperature of 200° to 800° C. for about 30 minutes to about 5 hours. The hydrogen reduction is usually carried out under the same conditions as described above.

The amount of copper and ruthenium contained in the catalyst is usually 0.1 to 30% by weight based on the weight of metal cobalt. The catalyst of the present invention may contain a compound such as chromium, manganese, and aluminum in addition to copper and ruthenium, and the amount of those compound is usually less than 10% by weight based on the weight of cobalt.

The amount of the alkali metal compound contained in the catalyst is usually 0.01 to 10% by weight and preferably 0.03 to 5% by weight in terms of alkali metal based on the total weight of catalyst.

Also, a lubricant such as graphite used at the time of catalyst pelleting can be used in the catalyst of the present invention.

The present invention is concerned with a process for producing an amine through a reductive amination of a cyclic ketone or reduction of an imino derivative of a cyclic ketone to a corresponding amine by using such a specific cobalt catalyst as described above.

The cyclic ketones and their imino derivatives may be cyclic compounds having a heteroatom and also may contain a substituent such as nitrile group and amino group. Specific examples of the compounds include, for example, cyclic ketones such as a alicyclic ketone having 5 to 20 carbon atoms such as cyclopentanone, cyclohexanone, cycloheptanone, isophorone, and 3-cyano-3,5,5-trimethylcyclohexanone (IPCN), heterocyclic ketones having 4 to 20 carbon atoms such as piperidone, 2,2,6,6-tetramethyl-4-piperidone, and 5-benzyl-7-oxo-5-azaspiro[2.4]heptane, and imino derivatives thereof, but the examples are not restricted to those compounds.

Among the compounds, the compounds having a nitrile group or amino group are preferably used. For instance, when 3-aminomethyl-3,5,5-trimethylcyclohexylamine (IPDA) is produced from IPCN or its imino derivative, the use of the above catalyst can repress by-production of, such as, 1,3,3-trimethyl-6-azabicyclo[3.2.1]octane (TMAB) which is supposed to be formed by intramolecular deamination of intermediates such as 3-iminomethyl-3,5,5-trimethylcyclohexylamine or 3-aminomethyl-3,5,5-trimethylcyclohexylamine.

In the reductive amination of a cyclic ketone or reduction of an imino derivative of a cyclic ketone, either reaction of a batch method or flow method can be adopted, but the latter is preferable. When the flow method is used, a fixed bed liquid-phase flow method is usually adopted which can be practiced either in up-flow or down-flow method.

The reaction temperature is usually 0° to 200° C. and preferably 30° to 150° C. The reaction pressure is usually from the pressure under which ammonia liquefies to 300 atm.

For the imination of a cyclic ketone and in order to prevent formation of by-products, ammonia is generally used in an amount of about 1.5 to 60 mols and preferably about 10 to about 50 mols per mol of the cyclic ketone or imino derivative of the cyclic ketone to be reduced.

The amount of the catalyst to be used is usually 0.01 to 5 times as much in weight as the material to be reduced, and the reaction time is usually about 30 minutes to about 10 hours in the batch method. In the flow method, the feeding rate of the solution of a material to be reduced is usually about 0.05 to about 10 $h^{-1}$ and preferably about 0.1 to about 5 $h^{-1}$ in LHSV. The reaction can be carried out even in the presence of a solvent. Such solvent includes alcohols such as methanol, ethanol, propanol, ethylene glycol, and ethylene glycol monomethyl ether, ethers such as diethyl ether, tetrahydrofuran, dioxane, and ethylene glycol dimethyl ether, hydrocarbons such as hexane and heptane, and mixtures of these solvents, with preferred being methanol.

The amount of the solvent when it is used is usually 0.5 to 10 times as much in weight as the material to be reduced.

The amount of hydrogen gas used is controlled by the reaction pressure in the case of batch method which is usually lower than 300 atm. In the case of the flow method, hydrogen gas is usually fed in an amount of 1 to 30 times as much in mol as the theoretical amount required for a material to be reduced.

When an amine is produced from a cyclic ketone, it is preferable from the view point of the yield of an objective product that ammonia is reacted with a cyclic ketone to form an imino derivative and then reducing the imino derivative.

When imino derivative is formed, the reaction is usually performed in the presence of a catalyst. As such catalyst, for example, an ion exchanger such as a sulfonated polystyrene (U.S. Pat. No. 4429157), acidic metal oxide such as alumina (Japanese Patent 4-221350A), metal complex oxide such as silica alumina, and active carbon can be mentioned.

Among them, active carbon is preferable. The active carbon may be one prepared from any of plants, coal, and petroleum, and the one having a large surface area is preferably used. Also, the active carbon treated either with an acid or alkali can be used.

In the imination, either a batch method or flow method can be adopted, but the latter is preferable. When the flow method is used, a fixed bed liquid-phase flow method is usually adopted, and the reaction can be performed either in up-flow method and down-flow method.

The reaction temperature is usually 0° to 100° C. The reaction pressure is usually from the pressure under which ammonia liquefies to about 300 atm. A specifically high pressure is not required, but it can be controlled to the same pressure as that in the succeeding hydrogenation step.

The amount of ammonia used is usually about 1 to about 60 mols per mol of the cyclic ketone. When considered the case where a reaction mass is supplied as it is to the succeeding hydrogenation step, the amount of ammonia used is preferably 2 to 50 mols per mol of the cyclic ketone.

The amount of an imination catalyst used is usually 1 to 25% by weight based on the weight of the cyclic ketone and the reaction time is usually about 5 minutes to about 3 hours in the case of the batch method. Also, in the case of the flow method, the flow rate of a ketone solution as a starting material is usually about 0.1 to about 10 $h^{-1}$ and preferably about 0.2 to about 5 $h^{-1}$ in LHSV.

The reaction in the imination can be carried out even in the presence of a solvent. Such solvent includes alcohols such as methanol, ethanol, propanol, ethylene glycol, and ethylene glycol monomethyl ether, ethers such as diethyl ether, tetrahydrofuran, dioxane, and ethylene glycol dimethyl ether, hydrocarbons such as hexane and heptane, and mixture of these solvents, with preferred being methanol.

The amount of the solvent when it is used is usually 0.5 to 10 parts by weight per part by weight of the cyclic ketone.

Thus, an imino derivative is formed. While the imino derivative is usually supplied from a reaction mass to the succeeding hydrogenation step as it is without isolation after the separation of the catalyst, it may be supplied after the isolation.

According to the present invention, amines can be efficiently produced from corresponding cyclic ketones or their imino derivatives at a high yield by using a cobalt catalyst containing a carbonate of an alkaline earth metal and/or lanthanum oxide.

EXAMPLES

The present invention will be described in further detail with reference to Examples. However, it should be understood that the invention is not limited to the specific Examples.

Catalyst Preparation Example 1

After 72.9 g of cobalt nitrate 6 hydrate and 2.9 g of copper nitrate 3 hydrate were dissolved in 300 ml of water to form a solution, 18.8 g of calcium carbonate was suspended in the solution, and the suspension was heated up to 80° C. Then, a solution comprised of 49.3 g of sodium carbonate in 300 ml of water was added dropwise to the suspension over 2 hours with stirring and the stirring was continued for 2 hours at the same temperature. After the precipitate thus formed was separated by filtration, it was washed 5 times with 500 ml of heated water at 80° C. Then, the precipitate was added to a solution of 1.9 g of sodium carbonate in 250 ml of water, the solution was concentrated with a rotary type evaporator, and the solid thus precipitated was subjected to a drying at 60° C. and grinding to obtain 48.7 g of a purple solid.

The purple solid in amount of 45 g was heated in a nitrogen gas stream at 320° C. for 1 hour, cooled down to an ambient temperature, and then taken out in air to obtain 37.0 g of a black solid. The Na content in the black solid was 1.9% by weight.

Then, after the black solid was granulated to 10 to 22 meshes (packing specific gravity=1.1), it was heated in a hydrogen gas stream at 280° C. for 5 hours to obtain cobalt catalyst A.

Catalyst Preparation Example 2

The procedures in Catalyst Preparation Example 1 were repeated except that the amount of 1.9 g of sodium carbonate which was used after washing the precipitate with heated water was decreased to 0.76 g to obtain cobalt catalyst B having a packing specific gravity of 1.1. The Na content in the catalyst was 0.9% by weight.

Catalyst Preparation Example 3

The procedures in Catalyst Preparation Example 1 were repeated except that the amount of 1.9 g of sodium carbonate which was used after washing the precipitate with heated water was decreased to 0.19 g to obtain cobalt catalyst C. having a packing specific gravity of 1. The Na content was 0.25% by weight.

Catalyst Preparation Example 4

The procedures in Catalyst Preparation Example 1 were repeated except that the precipitate was dried and ground without being treated with an aqueous solution of sodium carbonate after washing the precipitate with heated water to obtain cobalt catalyst D having a packing specific gravity of 1.1. The Na content was 0.06% by weight.

Catalyst Preparation Example 5

The procedures in Catalyst Preparation Example 1 were repeated except that 0.55 g of ruthenium chloride was used in place of copper nitrate, that the precipitate was dried and ground without being treated with an aqueous solution of sodium carbonate after washing the precipitate with heated water, and that the heating in a hydrogen gas stream was conducted at 380° C. for 5 hours to obtain cobalt catalyst E having a packing specific gravity of 1.1. The Na content was 0.045% by weight.

Catalyst Preparation Example 6

The procedures in Catalyst Preparation Example 1 were repeated except that a solution of 1.9 g of sodium hydroxide in 250 ml of water was used instead of a solution of 1.9 g of sodium carbonate in 250 ml of water after washing the precipitate with heated water to obtain cobalt catalyst F having a packing specific gravity of 1.1. The Na content was 2.63% by weight.

Catalyst Preparation Example 7

The procedures in Catalyst Preparation Example 1 were repeated except that a solution of 51.7 g of ammonium carbonate in 300 ml of water was used instead of a solution of 49.3 g of sodium carbonate in ml of water to form a precipitate and that the precipitate was dried and ground without being treated with an aqueous solution of sodium carbonate to obtain cobalt catalyst G having a packing specific gravity of 1.1. The content of Na was less than a detectable limit.

Catalyst Preparation Example 8

After 145.5 g of cobalt nitrate 6 hydrate was dissolved in 600 ml of water to form a solution, 37.5 g of calcium carbonate was suspended in the solution, and the suspension was heated up to 80° C. Then, after a solution of 93.8 g of sodium carbonate in 600 ml of water was added dropwise to the suspension over 2 hours with stirring, the stirring was continued for 2 hours at the same temperature. After the precipitate thus formed was separated by filtration, it was washed 5 times with 500 ml of heated water at 80° C. Then, after the precipitate was added to a solution of 3.75 g of sodium carbonate in 500 ml of water, the solution was concentrated with a rotary type evaporator, the solid was dried at 60° C. and grinding to obtain 94.7 g of a purple solid.

The purple solid in an amount of 45 g was heated in a nitrogen gas stream at 320° C. for 1 hour, cooled down to an ambient temperature, and then taken out in air to obtain 36.8 g of a black solid. The Na content in the black solid was 1.7% by weight.

Then, after the black solid was granulated into 10 to 22 meshes (packing specific gravity=1.1), it was calcined in a hydrogen gas stream at 380° C. for 5 hours to obtain cobalt catalyst H.

Catalyst Preparation Example 9

The procedures in Catalyst Preparation Example 8 were repeated except that the precipitate was dried and ground without being treated with an aqueous solution of sodium carbonate after washing the precipitate with heated water to obtain catalyst I having a packing specific gravity of 1. The Na content was 0.06% by weight.

Catalyst Preparation Example 10

The procedures in Catalyst Preparation Example 8 were repeated except that the heating temperature in a nitrogen gas stream was increased from 320° C. to 420° C. to obtain catalyst J having a packing specific gravity of 1.1. The Na content was 0.06% by weight.

Catalyst Preparation Example 11

The procedures in Catalyst Preparation Example 8 were repeated except that 3.75 g of sodium nitrate in 500 ml of water was used instead of a solution of 3.75 g of sodium carbonate in 500 ml of water was used to obtain catalyst K having a packing specific gravity of 1. The Na content was 1.17% by weight.

Catalyst Preparation Example 12

The procedures in Catalyst Preparation Example 8 were repeated except that 37.5 g of basic magnesium carbonate was used instead of calcium carbonate and that the precipitate was dried and ground without being treated with an aqueous solution of sodium carbonate after washing the precipitate with heated water to obtain catalyst L having a packing specific gravity of 0.7.

Catalyst Preparation Example 13

The procedures in Catalyst Preparation Example 8 were repeated except that 37.5 g of strontium carbonate was used instead of calcium carbonate and that the precipitate was dried and ground without being treated with an aqueous solution of sodium carbonate after washing the precipitate with heated water to obtain catalyst M having a packing specific gravity of 1.1.

Catalyst Preparation Example 14

The procedures in Catalyst Preparation Example 8 were repeated except that 37.5 g of barium carbonate was used instead of calcium carbonate and that the precipitate was dried and ground without being treated with an aqueous solution of sodium carbonate after washing the precipitate with heated water to obtain catalyst N having a packing specific gravity of 1.1.

Catalyst Preparation Example 15

The procedures in Catalyst Preparation Example 8 were repeated except that 37.5 g of lanthanum oxide was used instead of calcium carbonate and that the precipitate was dried and ground without being treated with an aqueous solution of sodium carbonate after washing the precipitate with heated water to obtain catalyst O having a packing specific gravity of 1.1.

Catalyst Preparation Example 16

After 72.9 g of cobalt nitrate 6 hydrate and 44.4 g of calcium nitrate were dissolved in 300 ml of water to form a solution, the solution was heated up to 80° C. Then, after a solution of 66.8 g of sodium carbonate in 300 ml of water was added dropwise to the nitrate solution over 2 hours with stirring, the stirring was continued for 2 hours at the same temperature. After the precipitate thus formed was separated by filtration, it was washed 5 times with 500 ml of heated water at 80° C. Then, after the precipitate was dried at 60° C. and ground, it was heated in a nitrogen gas stream and calcined in a hydrogen gas stream following the procedures in Catalyst Preparation Example 8 to obtain cobalt catalyst P having a packing specific gravity of 1. The Na content was 0.09% by weight.

Catalyst Preparation Example 17

The procedures in Catalyst Preparation Example 8 were repeated except that a solution of 100.3 g of ammonium carbonate in 600 ml of water was used instead of a solution of 93.8 g of sodium carbonate in 600 ml of water to form a precipitate and that the precipitate was dried and ground without being treated with an aqueous solution of sodium carbonate to obtain catalyst Q having a packing specific gravity of 1.3. The Na content was less than a detectable limit.

Catalyst Preparation Example 18

After 58.3 g of cobalt nitrate 6 hydrate was dissolved in 300 ml of water, it was heated up to 80° C. Then, after a solution of 37.5 g of sodium carbonate in 300 ml of water was added dropwise to the nitrate solution over 2 hours with stirring, the stirring was continued for 2 hours at the same temperature. After the precipitate thus formed was separated by filtration, it was washed 4 times with 500 ml of heated water at 80° C. to obtain purple solid.

Then, after the purple solid was suspended in 500 g of heated water at 80° C., 15 g of a silica gel (manufactured by Nippon Aerosil Co., Ltd.) was added to the suspension. The suspension was stirred to mix the solid and silica gel and they were separated from the liquid by filtration, dried at 60° C. and ground to obtain 36.2 g of another purple solid.

The latter purple solid in amount of 24.1 g was heated in a nitrogen gas stream at 330° C. for 1 hour, cooled down to an ambient temperature, and taken out in air to obtain 20.6 g of a black solid. Then, the black solid was granulated into 10 to 22 meshes (packing specific gravity=0.45) and calcined in a hydrogen gas stream at 380° C. for 5 hours to obtain cobalt catalyst R.

Catalyst Preparation Example 19

The procedures in Catalyst Preparation Example 18 were repeated except that 58.3 g of cobalt nitrate 6 hydrate and 3 g of manganese nitrate 6 hydrate were used instead of cobalt nitrate 6 hydrate to obtain cobalt catalyst S having a packing specific gravity of 0.45.

Catalyst Preparation Example 20

After 15.2 g of β-alumina and 0.92 g of ruthenium chloride were suspended in 150 ml of methanol, the suspension was stirred for 1 hour at an ambient temperature and then concentrated by using a rotary type evaporator to obtain 17.3 g of a yellowish brown solid. The solid was calcined in a nitrogen gas atmosphere at 120° C. to obtain 12.9 g of another yellowish brown solid.

Then, after the latter solid was granulated into 10 to 22 meshes (packing specific gravity=0.4), it was calcined in a hydrogen gas stream at 230° C. for 5 hours to obtain cobalt catalyst T.

Example 1

A stainless steel reaction tube (1) (80 cm in length, 9 mm in inside diameter) packed with 16.9 g of active carbon (24 to 48 meshes, GVA-S manufactured by Tsurumi Coal Co., Ltd) and a stainless steel reaction tube (2) (55 cm in length, 9 mm in inside diameter) packed with 20 ml of cobalt catalyst A previously reduced with hydrogen gas were vertically set and the top of the reaction tube (1) was connected with the bottom of the reaction tube (2). Then, a mixed liquid of 3-cyano-3,5,5-trimethylcyclohexanone (IPCN) with methanol at a weight ratio of 1:1.5 and liquid ammonia were fed at a rate of 34.7 g/h and 38.4 g/h, respectively, from the bottom of the reaction tube (1). Hydrogen gas was fed at a rate of 23.2 liter/h from the bottom of the reaction tube (2).

The inside temperature of the reaction tubes (1) and (2) were 24° C. and 121° C., respectively, and the reaction was performed while keeping the pressure in the reaction tubes (1) and (2) at 150 kg/cm$^2$G.

After lapse of 300 minutes from the starting of feeding, sampling was carried out from outlets of the reaction tubes (1) and (2) and the samples were analyzed by a gas chromatography.

The yield of the IPCN imino derivative at the outlet of the reaction tube (1) was 97.7%. The reaction mixture at the outlet of the reaction tube (2) contained 99.4% by weight of 3-aminomethyl-3,5,5-trimethylcyclohexylamine (IPDA) and 0.2% by weight of 3-aminomethyl-3,5,5-trimethylcyclohexyl alcohol (IPAA); IPCN and IPCN imino derivative were not detected; the content of 1,3,3-trimethyl-6-azabicyclo[3.2.1]octanol (TMAB) was 0.1% by weight and others was 0.3% by weight; and the yield of IPDA was 99.4%.

Example 2

The procedures in Example 1 were repeated except that a mixed liquid of IPCN with methanol at a weight ratio of 1:1.5, liquid ammonia, and hydrogen gas were fed at a rate of 23.3 g/h, 25.0 g/h, and 15.1 liter/h, respectively.

The yield of the IPCN imino derivative at the outlet of the reaction tube (1) was 97.7%. The reaction mixture at the outlet of the reaction tube (2) contained 99.3% by weight of IPDA and 0.5% by weight of IPAA; IPCN and IPCN imino derivatives were not detected; the content of TMAB was 0.2% by weight; and the yield of IPDA was 99.3%.

Example 3

The procedures in Example 1 were repeated except that a mixed liquid of IPCN with methanol at a weight ratio of 1:1.5, liquid ammonia, and hydrogen gas were fed at a rate of 10 g/h, 10 g/h, and 6 liter/h, respectively and that the pressure was kept at 70 kg/cm$^2$ G.

The yield of the IPCN imino derivative at the outlet of the reaction tube (1) was 98.3%. The reaction mixture at the outlet of the reaction tube (2) contained 97.6% by weight of IPDA and 1.6% by weight of IPAA; IPCN and IPCN imino derivative were not detected; the content of TMAB was 0.8% by weight; and the yield of IPDA was 97.6%.

Example 4

The procedures in Example 1 were repeated except that cobalt catalyst B was used in place of cobalt catalyst A.

The yield of the IPCN imino derivative at the outlet of the reaction tube (1) was 97.7%. The reaction mixture at the outlet of the reaction tube (2) contained 99.3% by weight of IPDA and 0.4% by weight of IPAA; IPCN and IPCN imino derivative were not detected; the content of TMAB was 0.2% by weight and others was 0.1% by weight; and the yield of IPDA was 99.2%.

Example 5

The procedures in Example 1 were repeated except that cobalt catalyst C. was used in place of cobalt catalyst A.

The yield of the IPCN imino derivative at the outlet of the reaction tube (1) was 97.8%. The reaction mixture at the outlet of the reaction tube (2) contained 98.7% by weight of IPDA and 0.4% by weight of IPAA; IPCN and IPCN imino derivative were not detected; the content of TMAB was 0.4% by weight and others was 0.5% by weight; and the yield of IPDA was 98.7%.

Example 6

The procedures in Example 1 were repeated except that cobalt catalyst D was used in place of cobalt catalyst A.

The yield of the IPCN imino derivative at the outlet of the reaction tube (1) was 98.9%. The reaction mixture at the outlet of the reaction tube (2) contained 98.5% by weight of IPDA and 0.5% by weight of IPAA; IPCN and IPCN imino derivative were not detected; the content of TMAB was 1.0% by weight; and the yield of IPDA was 98.4%.

Example 7

The procedures in Example 1 were repeated except that cobalt catalyst D was used in place of cobalt catalyst A and that a mixed liquid of IPCN with methanol at a weight ratio of 1:1.5, liquid ammonia, and hydrogen gas were fed at a rate of 23.3 g/h, 25 g/h, and 15 liter/h, respectively.

The yield of the IPCN imino derivative at the outlet of the reaction tube (1) was 99%. The reaction mixture at the outlet of the reaction tube (2) contained 99% of IPDA and 0.1% by weight of IPAA; IPCN and IPCN imino derivative were not detected; the content of TMAB was 0.9% by weight; and the yield of IPDA was 98.9%.

Example 8

The procedures in Example 1 were repeated except that cobalt catalyst E was used in place of cobalt catalyst A.

The yield of the IPCN imino derivative at the outlet of the reaction tube (1) was 98.8%. The reaction mixture at the outlet of the reaction tube (2) contained 97.7% by weight of IPDA and 1.5% by weight of IPAA; IPCN and IPCN imino derivative were not detected; the content of TMAB was 0.5% by weight and others was 0.3% by weight; and the yield of IPDA was 97.6%.

Example 9

The procedures in Example 1 were repeated except that cobalt catalyst F was used in place of cobalt catalyst A.

The yield of the IPCN imino derivative at the outlet of the reaction tube (1) was 98.2%. The reaction mixture at the outlet of the reaction tube (2) contained 97.2% by weight of IPDA and 2.6% by weight of IPAA; IPCN and IPCN imino derivative were not detected; the content of TMAB was 0.1% by weight and others was 0.1% by weight; and the yield of IPDA was 97.1%.

Example 10

The procedures in Example 1 were repeated except that cobalt catalyst G was used in place of cobalt catalyst A.

The yield of the IPCN imino derivative at the outlet of the reaction tube (1) was 97.6%. The reaction mixture at the outlet of the reaction tube (2) contained 95.8% by weight of IPDA and 2.8% by weight of IPAA; IPCN and IPCN imino derivative were not detected; the content of TMAB was 0.6% by weight and others was 0.8% by weight; and the yield of IPDA was 95.7%.

Example 11

The procedures in Example 1 were repeated except that cobalt catalyst H was used in place of cobalt catalyst A and that a mixed liquid of IPCN with methanol at a weight ratio of 1:1.5, liquid ammonia, and hydrogen gas were fed at a rate of 33.7 g/h, 38.4 g/h, and 23.2 liter/h, respectively.

The yield of the IPCN imino derivative at the outlet of the reaction tube (1) was 97.8%. The reaction mixture at the outlet of the reaction tube (2) contained 98.6% by weight of IPDA and 0.8% by weight of IPAA; IPCN and IPCN imino derivative were not detected; the content of TMAB was 0.1% by weight and others was 0.5% by weight; and the yield of IPDA was 98.6%.

Example 12

The procedures in Example 1 were repeated except that cobalt catalyst H was used in place of cobalt catalyst A and that a mixed liquid of IPCN with methanol at a weight ratio of 1:1.5, liquid ammonia, and hydrogen gas were fed at a rate of 23.7 g/h, 25.6 g/h, and 16.1 liter/h, respectively.

The yield of the IPCN imino derivative at the outlet of the reaction tube (1) was 97.8%. The reaction mixture at the outlet of the reaction tube (2) contained 99.3% by weight of IPDA and 0.6% by weight of IPAA; IPCN and IPCN imino derivative were not detected; the content of TMAB was 0.1% by weight; and the yield of IPDA was 99.3%.

Example 13

The procedures in Example 1 were repeated except that cobalt catalyst I was used in place of cobalt catalyst A and that a mixed liquid of IPCN with methanol at a weight ratio of 1:1.5, liquid ammonia, and hydrogen gas were fed at a rate of 24.4 g/h, 26.5 g/h, and 15 liter/h, respectively.

The yield of the IPCN imino derivative at the outlet of the reaction tube (1) was 99.2%. The reaction mixture at the outlet of the reaction tube (2) contained 98.6% by weight of IPDA and 0.7% by weight of IPAA; IPCN and IPCN imino derivative were not detected; the content of TMAB was 0.6% by weight and others was 0.1% by weight; and the yield of IPDA was 98.5%.

Example 14

The procedures in Example 1 were repeated except that cobalt catalyst I was used in place of cobalt catalyst A, that a mixed liquid of 2,2,6,6-tetramethyl-4-piperidone (TMP) with methanol at a weight ratio of 1:1.5 was used instead of a mixed liquid of IPCN with methanol, and that the mixed liquid of TMP with methanol, liquid ammonia, and hydrogen gas were fed at a rate of 10 g/h, 10 g/h, and 6 liter/h, respectively.

The yield of the TMP imino derivative at the outlet of the reaction tube (1) was 94.9%. In the reaction liquid at the outlet of the reaction tube (2), TMP imino derivative and TMP were not detected; and the yield of amino derivative of TMP was 94.7%.

Example 15

The procedures in Example 1 were repeated except that cobalt catalyst J was used in place of cobalt catalyst A and that a mixed liquid of IPCN with methanol at a weight ratio of 1:1.5, liquid ammonia, and hydrogen gas were fed at a rate of 23.3 g/h, 25 g/h, and 15 liter/h, respectively.

The yield of the IPCN imino derivative at the outlet of the reaction tube (1) was 98.6%. The reaction mixture at the outlet of the reaction tube (2) contained 98.1% by weight of IPDA and 1.2% by weight of IPAA; IPCN and IPCN imino derivative were not detected; the content of TMAB was 0.7% by weight; and the yield of IPDA was 98%.

Example 16

The procedures in Example 1 were repeated except that cobalt catalyst K was used in place of cobalt catalyst A.

The yield of the IPCN imino derivative at the outlet of the reaction tube (1) was 97.6%. The reaction mixture at the outlet: of the reaction tube (2) contained 96.1% by weight of IPDA and 3.1% by weight of IPAA; IPCN and IPCN imino derivative were not detected; the content of TMAB was 0.4% by weight and others was 0.4% by weight; and the yield of IPDA was 96.1%.

Example 17

The procedures in Example 1 were repeated except that cobalt catalyst L was used in place of cobalt catalyst A.

The yield of the IPCN imino derivative at the outlet of the reaction tube (1) was 97.5%. The reaction mixture at the outlet of the reaction tube (2) contained 95.6% by weight of IPDA and 1.6% by weight of IPAA; IPCN and IPCN imino derivative were not detected; the content of TMAB was 2.8% by weight; and the yield of IPDA was 95.2%.

Example 18

The procedures in Example 1 were repeated except that cobalt catalyst M was used in place of cobalt catalyst A.

The yield of the IPCN imino derivative at the outlet of the reaction tube (1) was 97.4%. The reaction mixture at the outlet of the reaction tube (2) contained 98.5% by weight of IPDA and 0.2% by weight of IPAA; IPCN and IPCN imino derivative were not detected; the content of TMAB was 0.2% by weight and others was 1.1% by weight; and the yield of IPDA was 98.5%.

Example 19

The procedures in Example 1 were repeated except that cobalt catalyst N was used in place of cobalt catalyst A.

The yield of the IPCN imino derivative at the outlet of the reaction tube (1) was 97.8%. The reaction mixture at the outlet of the reaction tube (2) contained 97.6% by weight of IPDA and 0.3% by weight of IPAA; IPCN and IPCN imino derivative were not detected; the content of TMAB was 0.6% by weight and others was 1.5% by weight; and the yield of IPDA was 97.5%.

Example 20

The procedures in Example 1 were repeated except that cobalt catalyst O was used in place of cobalt catalyst A and that a mixed liquid of IPCN with methanol at a weight ratio of 1:1.5, liquid ammonia, and hydrogen gas were fed at a rate of 23.3 g/h, 25 g/h, and 15 liter/h, respectively.

The yield of the IPCN imino derivative at the outlet of the reaction tube (1) was 98%. The reaction mixture at the outlet of the reaction tube (2) contained 95.5% by weight of IPDA and 3.4% by weight of IPAA; IPCN and IPCN imino derivative were not detected; the content of TMAB was 1.1% by weight; and the yield of IPDA was 95.4%.

Example 21

The procedures in Example 1 were repeated except that cobalt catalyst P was used in place of cobalt catalyst A and that a mixed liquid of IPCN with methanol at a weight ratio of 1:1.5, liquid ammonia, and hydrogen gas were fed at a rate of 23.3 g/h, 25 g/h, and 15 liter/h, respectively.

The yield of the IPCN imino derivative at the outlet of the reaction tube (1) was 98.4%. The reaction mixture at the outlet of the reaction tube (2) contained 97.2% by weight of IPDA and 1.7% by weight of IPAA; IPCN and IPCN imino derivative were not detected; the content of TMAB was 0.9% by weight and others was 0.2% by weight; and the yield of IPDA was 97.2%.

Example 22

The procedures in Example 1 were repeated except that cobalt catalyst Q was used in place of cobalt catalyst A and that a mixed liquid of IPCN with methanol at a weight ratio of 1:1.5, liquid ammonia, and hydrogen gas were fed at a rate of 23.3 g/h, 25 g/h, and 15 liter/h, respectively.

The yield of the IPCN imino derivative at the outlet of the reaction tube (1) was 98.4%. The reaction mixture at the outlet of the reaction tube (2) contained 95.5% by weight of IPDA and 2.9% by weight of IPAA; IPCN and IPCN imino derivative were not detected; the content of TMAB was 1.4% by weight and others was 0.2% by weight; and the yield of IPDA was 95.4%.

Example 23

A stainless steel reaction tube (55 cm in length, 9 mm in inside diameter) packed with 20 ml of cobalt catalyst I previously reduced by hydrogen gas was vertically set and a mixed liquid of IPCN with methanol and liquid ammonia at a weight ratio of 1:1.5:2.5 was fed from the bottom of the reaction tube at a rate of 51.2 g/h. Also, hydrogen gas was fed from the bottom of the reaction tube at a rate of 15.1 liter/h. The inside temperature of the reaction tube was 121° C. and the reaction pressure was kept at 150 kg/cm$^2$G.

After lapse of 300 minutes from the starting of feeding, the reaction mixture at an outlet of the reaction tube contained 84.8% by weight of IPDA and 14% by weight of IPAA; IPCN and IPCN imino derivative were not detected; the content of TMAB was 1.2% by weight; and the yield of IPDA was 84.8%.

Comparative Example 1

The procedures in Example 1 were repeated except that cobalt catalyst R was used in place of cobalt catalyst A and that a mixed liquid of IPCN with methanol at a weight ratio of 1:1.5, liquid ammonia, and hydrogen gas were fed at a rate of 24.5 g/h, 25.3 g/h, and 15 liter/h, respectively.

The yield of the IPCN imino derivative at the outlet of the reaction tube (1) was 99.2%. The reaction mixture at the outlet of the reaction tube (2) contained 91.0% by weight of IPDA and 5.8% by weight of IPAA; IPCN and IPCN imino derivative were not detected; the content of TMAB was 3.2% by weight; and the yield of IPDA was 90.7%.

Comparative Example 2

The procedures in Example 1 were repeated except that cobalt catalyst S was used in place of cobalt catalyst A and that a mixed liquid of IPCN with methanol at a weight ratio of 1:1.5, liquid ammonia, and hydrogen gas were fed at a rate of 24.5 g/h, 25.3 g/h, and 15 liter/h, respectively.

The yield of the IPCN imino derivative at the outlet of the reaction tube (1) was 97.9%. The reaction mixture at the outlet of the reaction tube (2) contained 89.9% by weight of IPDA and 6.3% by weight of IPAA; IPCN and IPCN imino derivative were not detected; the content of TMAB was 3.8% by weight; and the yield of IPDA was 89.6%.

Comparative Example 3

The procedures in Example 1 were repeated except that cobalt catalyst T was used in place of cobalt catalyst A.

The yield of the IPCN imino derivative at the outlet of the reaction tube (1) was 99.2%. The reaction mixture at the outlet of the reaction tube (2) contained 71.8% by weight of IPDA and 9.4% by weight of IPAA; IPCN and IPCN imino derivative were not detected; the content of TMAB was 10.8% by weight and others was 7% by weight; and the yield of IPDA was 71.8%.

Comparative Example 4

The procedures in Example 23 were repeated except that cobalt catalyst R was used in place of cobalt catalyst I.

The reaction mixture at the outlet of the reaction tube contained 76.5% by weight of IPDA and 19.5% by weight of IPAA; IPCN and IPCN imino derivative were not detected; the content of TMAB was 4% by weight; and the yield of IPDA was 76.3%.

We claim:

1. A process for producing an amine by carrying out a reductive amination of a cyclic ketone or by carrying out a reduction of an imino derivative of a cyclic ketone to the corresponding amine which comprises carrying out the reductive amination or reduction in the presence of a cobalt catalyst containing a carbonate of an alkaline earth metal and/or lanthanum oxide on which cobalt is supported.

2. The process according to claim 1 wherein the amount of the carbonate of an alkaline earth metal and/or lanthanum oxide to metal cobalt is 10/90 to 98/2 by weight ratio.

3. The process according to claim 1 wherein the carbonate of an alkaline earth metal is at least one compound selected from the group consisting of a carbonate of magnesium, calcium, strontium, or barium.

4. The process according to claim 1 wherein the carbonate of an alkaline earth metal is calcium carbonate.

5. The process according to claim 1 wherein the cobalt catalyst further contains copper and/or ruthenium.

6. The process according to claim 5 wherein the amount of the copper and/or ruthenium contained in the catalyst is 0.1 to 30% by weight based on the weight of metal cobalt.

7. The process according to claim 1 or 5 wherein the cobalt catalyst further contains an alkali metal compound.

8. The process according to claim 7 wherein the amount of the alkali metal compound contained in the catalyst is 0.01 to 10% by weight in terms of alkali metal based on the total weight of the catalyst.

9. The process according to claim 1 wherein the cobalt catalyst is prepared by a precipitation, coprecipitation, mixing, or impregnation method.

10. The process according to claim 9 wherein the cobalt catalyst to be prepared by the precipitation method is prepared by suspending a carbonate of an alkaline earth metal in a solution in which a cobalt salt is dissolved, adding a solution of an alkali to the suspension to precipitate the cobalt on the carbonate of an alkaline earth metal, and then subjecting the cobalt and carbonate to filtration, washing, drying, and reducing with hydrogen.

11. The process according to claim 9 wherein the cobalt catalyst to be prepared by the coprecipitation method is prepared by adding a solution of a carbonate of an alkali metal or ammonium carbonate to a mixed solution of a cobalt salt and an alkaline earth metal to form a coprecipitate and then subjecting the coprecipitate to filtration, washing, drying, and reducing with hydrogen.

12. The process according to claim 9 wherein the cobalt catalyst to be prepared by the mixing method is prepared by adding a solution of an alkali to a solution in which a cobalt salt is dissolved to form a precipitate, adding a carbonate of an alkaline earth metal to the solution, mixing the precipitate in the solution and carbonate, and then subjecting the mixture to filtration, washing, drying, and reducing with hydrogen.

13. The process according to claim 9 wherein the cobalt catalyst to be prepared by the impregnation method is prepared by impregnating a carbonate of an alkaline earth metal with a solution in which a cobalt salt is dissolved and then subjecting the impregnated carbonate to drying, calcination, and reducing with hydrogen.

14. The process according to claim 1 wherein the cyclic ketone is an alicyclic ketone having 5 to 20 carbon atoms or a heterocyclic ketone having 4 to 20 carbon atoms.

15. The process according to claim 14 wherein the alicyclic ketone is at least one compound selected from the group consisting of cyclopentanone, cyclohexanone, cycloheptanone, isophorone, and 3-cyano-3,5,5-trimethylcyclohexanone.

16. The process according to claim 14 wherein the alicyclic ketone is 3-cyano-3,5,5-trimethylcyclohexanone.

17. The process according to claim 14 wherein the heterocyclic ketone is at least one compound selected from the group consisting of piperidone, 2,2,6,6-tetramethyl-4-piperidone, and 5-benzyl-7-oxo-5-azaspiro[2.4]heptane.

18. The process according to claim 14 wherein the heterocyclic ketone is 2,2,6,6-tetramethyl-4-piperidone.

19. The process according to claim 1 wherein the imino derivative of a cyclic ketone is an imino derivative of an alicyclic ketone having 5 to 20 carbon atoms or an imino derivative of a heterocyclic ketone having 4 to 20 carbon atoms.

20. The process according to claim 19 wherein the imino derivative of an alicyclic ketone is at least one compound selected from the group consisting of an imino derivative of cyclopentanone, cyclohexanone, cycloheptanone, isophorone, or 3-cyano-3,5,5-trimethylcyclohexanone.

21. The process according to claim 19 wherein the imino derivative of an alicyclic ketone is an imino derivative of 3-cyano-3,5,5-trimethylcyclohexanone.

22. The process according to claim 19 wherein the imino derivative of a heterocyclic ketone is at least one compound selected from the group consisting of an imino derivative of piperidone, 2,2,6,6-tetramethyl-4-piperidone, or 5-benzyl-7-oxo-5-azaspiro[2.4]heptane.

23. The process according to claim 19 wherein the imino derivative of a heterocyclic ketone is an imino derivative of 2,2,6,6-tetramethyl-4-piperidone.

24. The process according to claim 1 wherein the reductive amination or reduction is carried at a temperature of 0 to 200° C. and under a pressure in the range of from the pressure under which ammonia liquefies to 300 atm.

25. The process according to claim 1 wherein ammonia is used in an amount of 1.5 to 60 mols per mol of the cyclic ketone or imino derivative thereof.

26. The process according to claim 1 wherein the cobalt catalyst is used in an amount of 0.01 to 5 parts by weight per part by weight of the cyclic ketone or imino derivative thereof.

27. The process according to claim 1 wherein a feed rate of the cyclic ketone or imino derivative thereof is 0.05 to 10 $h^{-1}$ in LHSV.

28. The process according to claim 1 wherein the reductive amination or reduction is carried out in the presence of an alcohol, ether, or hydrocarbon type solvent, or their mixture.

29. The process according to claim 28 wherein the alcohol type solvent is methanol.

30. A process according to claim 1, wherein reductive amination of cyclic ketones or reduction of imino derivatives of the cyclic ketones is carried out in the presence of 1.5–60 mol of ammonia per mol of the cyclic ketones or imino derivatives thereof, and 0.01–5 parts by weight of cobalt catalysts per part by weight of the cyclic ketones or imino derivatives thereof, under 300 atm or smaller of hydrogen pressure.

31. A process according to claim 1, wherein reductive amination of cyclic ketones or reduction of imino derivatives of cyclic ketones is carried out in the presence of 1.5–60 mol of ammonia per mol of the cyclic ketones or imino derivatives thereof, and 1–30 times in mol of hydrogen gas as much as an amount theoretically required for materials to be reduced, under 0.05–10 $hr^{-1}$ in LHSV of feeding speed of the cyclic ketones or imino derivatives thereof.

32. A process according to claim 1, wherein the cobalt catalyst contains lanthanum oxide.

* * * * *